United States Patent
Giencke (12)

(10) Patent No.: US 9,864,075 B2
(45) Date of Patent: Jan. 9, 2018

(54) INTEGRATED RECIPROCAL SPACE MAPPING FOR SIMULTANEOUS LATTICE PARAMETER REFINEMENT USING A TWO-DIMENSIONAL X-RAY DETECTOR

(71) Applicant: Bruker AXS, Inc., Madison, WI (US)

(72) Inventor: Jonathan Giencke, Verona, WI (US)

(*) Notice: Subject to any disclaimer, the term of this patent is extended or adjusted under 35 U.S.C. 154(b) by 594 days.

(21) Appl. No.: 14/289,336

(22) Filed: May 28, 2014

(65) Prior Publication Data

US 2015/0346121 A1 Dec. 3, 2015

(51) Int. Cl.
*G01T 1/29* (2006.01)
*G01B 9/10* (2006.01)
(Continued)

(52) U.S. Cl.
CPC ........ *G01T 1/2978* (2013.01); *G01B 9/02018* (2013.01); *G01B 9/02019* (2013.01);
(Continued)

(58) Field of Classification Search
CPC .. G01N 23/00; G01N 23/20; G01N 23/20008; G01N 23/20016; G01N 23/20091; G01N 23/205; G01N 23/2055; G01N 23/207; G01N 2223/00; G01N 2223/05; G01N 2223/0569; G01N 2223/0561; G01N 2223/0563; G01N 2223/0566; G01N 2223/60; G01N 2223/602–2223/605; G01N 2223/61; G01N 15/00; G01N 15/02; G01N 15/0205; G01N 15/0211; G01N 21/00; G01N 21/47; G01N 21/4738; G01N 21/4788; G01N 21/62; G01N 21/63; G01N 21/84; G01N 21/8422; G01N 2021/00; G01N 2021/848;
(Continued)

(56) References Cited

U.S. PATENT DOCUMENTS

2002/0197501 A1* 12/2002 Robbins ................ C23C 14/165
428/621
2003/0009316 A1* 1/2003 Yokoyama ............. G01N 23/20
703/2

(Continued)

OTHER PUBLICATIONS

Schmidbauer, M. et al., A novel multi-detection technique for three-dimensional reciprocal-space mapping in grazing-incidence X-ray diffraction, J. Synchrotron Rad. (2008), vol. 15, pp. 549-557, International Union of Crystallography.

(Continued)

*Primary Examiner* — Anastasia Midkiff
(74) *Attorney, Agent, or Firm* — Benoît & Côté Inc.

(57) ABSTRACT

A method for performing an X-ray diffraction analysis of a crystal sample using a multi-dimensional detector that integrates an X-ray diffraction signal while the position of the sample relative to an X-ray source is changed along a scan direction. The resulting image is compressed along the scan direction, but may be collected very quickly. The capture of both on-axis and off-axis reflections in a single image provides a common spatial frame of reference for comparing the reflections. This may be used in the construction of a reciprocal space map, and is useful for analyzing a sample with multiple crystal layers, such as a crystal substrate with a crystalline film deposited thereupon.

16 Claims, 4 Drawing Sheets

(51) Int. Cl.
*G01B 15/00* (2006.01)
*G01N 23/20* (2006.01)
*G01N 15/02* (2006.01)
*G01N 23/207* (2006.01)
*G01B 9/02* (2006.01)
*G01N 21/84* (2006.01)

(52) U.S. Cl.
CPC .......... *G01B 9/02041* (2013.01); *G01B 9/10* (2013.01); *G01N 15/0211* (2013.01); *G01N 23/207* (2013.01); *G01N 23/20008* (2013.01); *G01N 23/20016* (2013.01); *G01B 15/00* (2013.01); *G01B 2290/65* (2013.01); *G01N 2021/8477* (2013.01); *G01N 2223/0561* (2013.01); *G01N 2223/0566* (2013.01); *G01N 2223/331* (2013.01); *G01N 2223/61* (2013.01)

(58) Field of Classification Search
CPC ....... G01N 2021/8477; G01N 2015/00; G01N 2015/0216; G01N 2015/025; G01N 33/00; G01N 33/38; G01N 33/385; G01B 9/00; G01B 9/02; G01B 9/02015–9/02019; G01B 9/02029; G01B 9/0203; G01B 9/02041; G01B 9/02087; G01B 9/0209; G01B 9/10; G01B 11/00; G01B 11/08; G01B 11/12; G01B 15/00; G01B 2290/00; G01B 2290/65; G06F 7/00; G06F 7/72; G06F 7/721; G06F 7/724; G06F 7/726; G06F 2101/00; G06F 2101/12; G01T 1/00; G01T 1/29; G01T 1/2914; G01T 1/2978

See application file for complete search history.

(56) References Cited

U.S. PATENT DOCUMENTS

| | | | |
|---|---|---|---|
| 2005/0024646 A1* | 2/2005 | Quadling | A61B 5/0066 356/477 |
| 2007/0020891 A1* | 1/2007 | Kouvetakis | B82Y 10/00 438/479 |
| 2011/0187237 A1* | 8/2011 | Suenaga | H01L 41/187 310/363 |
| 2012/0176626 A1* | 7/2012 | Quadling | A61B 5/0066 356/511 |
| 2012/0257197 A1* | 10/2012 | Feldkhun | G01N 21/4795 356/301 |
| 2013/0103339 A1 | 4/2013 | Durst et al. | |

OTHER PUBLICATIONS

Chahine, Gilbert André, et al., Imaging of strain and lattice orientation by quick scanning X-ray microscopy combined with three-dimensional reciprocal space mapping, Journal of Applied Crystallography, vol. 33, No. 2, Apr. 4, 2014, pp. 762-769, International Union of Crystallography.

* cited by examiner

INTEGRATED RECIPROCAL SPACE MAPPING FOR SIMULTANEOUS LATTICE PARAMETER REFINEMENT USING A TWO-DIMENSIONAL X-RAY DETECTOR

BACKGROUND OF THE INVENTION

Field of the Invention

This invention relates generally to the field of X-ray diffraction crystallography and, more specifically, to the measurement of lattice parameters in an X-ray diffraction crystallography experiment.

Description of the Related Art

When a beam of radiation with wavelength on the order of the spacing between atoms is made incident upon a crystalline material, several interferometrically reinforced beams are emitted from the sample when the proper geometry of the incident beam relative to the spacing of interest is attained. The condition in which diffraction occurs was described by Bragg as $\lambda=2d \sin \theta$, where $\lambda$ represents the wavelength of radiation used, d represents the interatomic spacing and $\theta$ represents the angle at which the beam is made incident upon the crystal. To reach the diffracting condition for a specific crystallographic plane of interest, knowledge of the crystal system must be combined with knowledge of the motion of a goniometer in which the crystal is mounted, a method described by Paul Ewald with his construction of the Ewald Sphere in Reciprocal Space.

In an Ewald Sphere construction, the diffracting condition is represented by a sphere of radius $1/\lambda$. This sphere intersects the origin of reciprocal space at one point on its surface. The reciprocal lattice, in which the Ewald Sphere is constructed, has axes which are related to the real space distance between atomic planes through an inverse relationship. The real space motions of an X-Ray Diffractometer result in the Ewald sphere being rotated in an analogous fashion in reciprocal space. When a reciprocal lattice point, whose shape and location are defined by the structure of the crystalline sample, in reciprocal space intersects the Ewald sphere, the condition is met such that a reinforcement of the scattered radiation (with wavelength equal to that of the incident beam) leaving the sample occurs. This is commonly referred to as a "reflection." By manipulating the orientation of a detector relative to the crystal, that beam can be captured, and its relative coordinates used to determine the atomic spacings in the material. It is common practice to collect an extensive number of these data points, and map them in what is called a "reciprocal space map."

In conventional systems, the construction of a reciprocal space map makes use of either a point detector or a one-dimensional (1D) detector to collect the data related to the reciprocal lattice. Thus, for each orientation of the sample, the detector is moved relative to the sample to cover all regions of interest where there might be a reflection. Once reflection data has been gathered over a large range of orientations, a reciprocal space map may be assembled. However, depending on the number of points being sampled, the process may take hours, or even days, to complete.

While crystal samples may take different forms, one particular structure of interest is a material having two different crystal layers, such as a crystal substrate with a film of crystal material deposited on it. For a structure such as this, rotation of the sample (and corresponding rotation of the Ewald sphere) results in reflections being generated from both the substrate layer and the film layer. By measuring several reflections associated with the crystal structure of the substrate and film, properties of the real space crystal structure, such as the spacing of atoms normal to the surface of the crystal, spacing of the atoms in the plane of the surface of the crystal and the relationship of the film crystal structure to the substrate crystal structure, can be determined. This is done conventionally with a zero-dimensional (point) or one-dimensional (line) detector, which collects a series of points that are post-processed into a planar cross-sectional map through reciprocal space for each of the materials.

SUMMARY OF THE INVENTION

In accordance with the present invention, a method is provided for performing an X-ray diffraction analysis of a crystal sample that uses a multi-dimensional X-ray detector and that integrates a diffracted X-ray signal along the extent of the X-ray scan. The sample is irradiated with an X-ray beam from an X-ray source, and the diffracted X-ray signal is detected with the detector, which may be a two-dimensional area detector, and which has a fixed position relative to the X-ray source. The position of the sample relative to the X-ray source is then changed along a scan direction while integrating the detected X-ray diffraction signal with the detector so as to produce a multi-dimensional image that is compressed in the scan direction. The image data may be used, for example, in constructing a reciprocal space map of the sample material.

In an exemplary embodiment of the invention, the scan direction is the rocking direction of a goniometer in which the sample is mounted, and relative movement of the sample and the X-ray source results in the image being compressed along the rocking direction. The diffracted X-ray signal detected by the detector may also include reflections originating from atomic planes with orientation parallel to the crystal surface, also known as "on-axis" reflections, or atomic planes tilted relative to the crystal surface, also known as "off-axis" reflections. In an exemplary embodiment of the invention, the on-axis reflections lie along a central axis of detection in the multi-dimensional image, while the off-axis reflections are offset from the central axis. The analysis may include identifying Miller indices for the on-axis and off-axis reflections, and determining a relative crystal orientation of the crystal sample by comparing the Miller indices.

In certain cases, the sample may comprise a plurality of different crystal materials, such as a substrate layer of a first material and a film layer of a second material. Thus, the reflections from both layers are present in the same image, and a spatial relationship between them can therefore be deduced using the multi-dimensional detector as a common frame of reference. On-axis and off-axis reflections may be collected from each of the layers, and data from the multi-dimensional image may be integrated in a direction perpendicular to the central axis of detection to produce a one-dimensional representation of the on-axis and off-axis reflections from each of the crystal materials. If one of the layers is a known reference layer, the one-dimensional representation may be analyzed to determine the on-axis and off-axis lattice parameters of a second layer.

In the specific embodiment for which the sample includes a plurality of crystal layers each with a different crystalline structure, the method again includes illuminating the sample material with an X-ray beam from an X-ray source. A multi-dimensional X-ray detector having a fixed position relative to the source is used to detect a diffracted X-ray signal emitted from the sample, such that X-ray reflections originating from each of the crystal layers are detected at different spatial positions on the X-ray detector. The position of the sample relative to the X-ray source is then changed along a scan direction while integrating the detected X-ray reflection signal with the detector so as to produce a multi-dimensional image that is compressed in the scan direction. The reflections within the image that originate from different crystal layers are then compared to determine a corresponding spatial relationship between the crystalline layers of the sample.

In the foregoing embodiment, the scan direction may be the rocking direction of a goniometer in which the sample is mounted, and the multi-dimensional X-ray image may be used to construct a reciprocal space map. As with other embodiments, the diffracted X-ray signal may include both on-axis and off-axis reflections, and the different crystal layers may include a substrate layer of a first material and a film layer of a second material different from the first material. In one example of this embodiment, the reflections of a known substrate material captured by the detector may be used as an internal reference for refinement of the lattice parameters of an unknown film layer.

DETAILED DESCRIPTION

Figure 1:
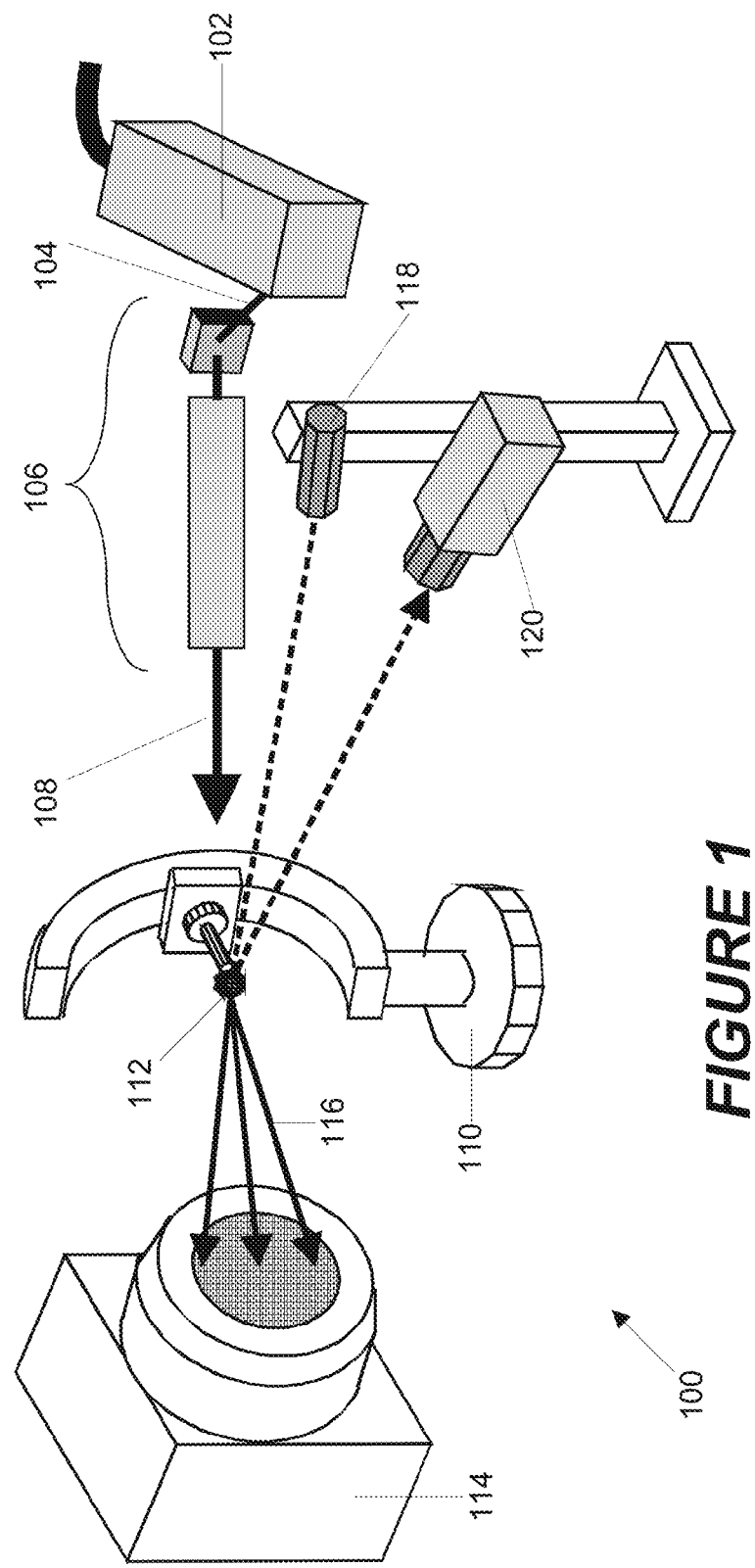
FIG. 1 is a perspective view of a diffractometry system that may be used with the present invention.

Shown in FIG. 1 is a schematic depiction of a diffractometry system 100 that may be used with the present invention. The components of the system include an X-ray source 102 that produces a primary X-ray beam 104 with the required radiation energy, focal spot size and intensity. X-ray optics 106 are provided to condition the primary X-ray beam 104 to a conditioned, or incident, beam 108 with the required wavelength, beam focus size, beam profile and divergence. A goniometer 110 is used to establish and manipulate geometric relationships between the incident X-ray beam 108, the crystal sample 112 and the X-ray sensor 114. The incident X-ray beam 108 strikes the crystal sample 112 and produces scattered X-rays 116 which are recorded in the sensor 114. An optional sample alignment and monitor assembly comprises a sample illuminator 118 that illuminates the sample 112 and a sample monitor 120, typically a video camera, which generates a video image of the sample to assist users in positioning the sample in the instrument center and monitoring the sample state and position.

In conventional X-ray analysis, the construction of a reciprocal space map may involve the collection of images at a series of rotational positions along the beam "rocking direction." In such an analysis, the goniometer is operated to change the angle of incidence of the X-ray beam relative to the sample, while maintaining the angle between the beam source and the detector. For example, the sample may be stationary, while the X-ray source and the detector are moved incrementally in unison along a circular path surrounding the sample. At each increment, an image is collected with the detector and stored, and the collected images are subsequently processed to create a three-dimensional representation indicative of the reciprocal lattice. While such a method can produce an accurate result, it is a time-consuming and data intensive process.

In an exemplary embodiment of the invention, a two-dimensional detector is used to collect reflection data along the beam rocking direction but, rather than collecting individual image frames, the reflection data is integrated as the relative position of the detector and the sample changes. Thus, for example, the sample may be kept stationary while the X-ray source and the detector move in unison along the beam rocking direction. During this motion, the detector integrates the reflection signals that are produced, resulting in a single two-dimensional image that is compressed in the beam rocking direction.

Figure 2:
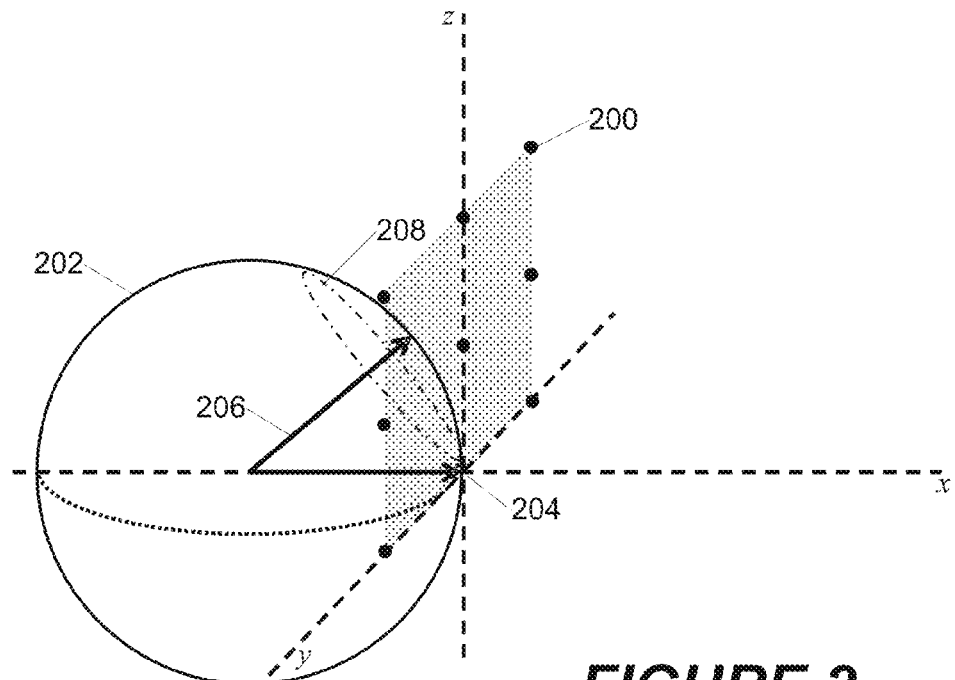
FIG. 2 is a schematic depiction of the movement of an Ewald sphere relative to a reciprocal lattice in a diffractometry scan according to the present invention.

The effect of using a two-dimensional detector in the construction of a reciprocal space map is demonstrated by the schematic depiction shown in FIG. 2. For a single crystal sample mounted in a goniometer, changing the direction of the incident beam relative to the sample while maintaining a constant angle between the incident beam direction and the position of the detector results in a rotation of the Ewald sphere in reciprocal space. Thus, for a given plane 200 in the reciprocal lattice, the Ewald sphere 202 will rotate about the origin 204 of the coordinate system. The angle 206 is composed of two lines, one being from the center of the Ewald sphere to the origin of the reciprocal lattice, and the other being from the origin of the sphere to the center of the detection plane. The angle between these two lines is equal to the $\alpha$-angle of the diffractometer, which is defined by the direction of the incident X-ray beam and a line between the sample and the center of the detector. This corresponds to the $2\theta$ angle of the diffractometer although, since a two-dimensional detector is used, reflections are detected along a finite range of possible $2\theta$ angles.

As shown in the diagram of FIG. 2, the center of the detection plane will determine the center of the section 208 of the Ewald sphere that is covered by the two-dimensional surface of the detector. As the Ewald sphere 202 rotates in reciprocal space within the plane defined by the angle 206, it intersects lattice points in the plane 200, and those lattice points that intersect the region of the Ewald sphere falling within the section 208 will correspond to reflections that are detected by the detector in real space. These reflections will appear and disappear at the surface of the detector as the system passes in and out of a diffracting condition with different planes of the crystal. However, since the detection of these reflections is integrated over the entire range of movement, all of the reflection data is represented in a single detector image. This "compression" of the scan along the beam rocking direction allows for a rapid collection of data within the two-dimensional range of the detector, but information regarding the discrimination of reflection data in the perpendicular dimension is lost. This differs from a conventional rocking beam curve analysis, in which a series of images is collected at each of many incremental positions along the rocking beam direction. The individual images of such an analysis allow for the shape of reflections in the direction of the scan to be determined. However, such an analysis is also very time-consuming and data intensive. In contrast, the method of the present invention is very fast. Moreover, as most reflections are symmetrical in nature, the shape of the reflection in the plane of the detector often provides sufficient information regarding the reflection shape.

Referring again to FIG. 2, a single detector image collected using the present invention will include multiple reflections that correspond to different lattice points in the plane 200. These will include "on-axis" reflections that lie along the plane of rotation which, in the coordinate system of FIG. 2, is the x-z plane. However, as the section 208 of the Ewald sphere that is covered by the two-dimensional detector extends beyond this plane, "off-axis" reflections, i.e., those not within the plane of rotation, will also be detected. Because of the curvature of the Ewald sphere, the on-axis and off-axis reflections collected in the detector image will not have a linear positional relationship relative to one another. However, they nonetheless reside within the same frame of reference in the image and have a relative spatial distribution that is indicative of the structure of the reciprocal lattice. With appropriate knowledge of the crystal structure and the parameters of the diffractometer system, the various detected reflections can be used in the construction of a reciprocal space map.

As is known in the art, the reciprocal lattice points that are in the plane of rotation, such as the x-z plane shown in FIG. 2, correspond to reflections from the 00L series of planes. This series of planes may be representative, for example, of one dimension (i.e., the "height") of the unit cell for the crystal. Thus, as the Ewald sphere is rotated as shown in FIG. 2, these on-axis lattice points along the z-axis are encountered, and the reflections generated as a result will be detected. As mentioned above, reflections corresponding to off-axis lattice points to either side of the z-plane are also detected. These reflections are indicative of other lattice parameters, such as the "width" of the unit cell for the crystal. Thus, given an appropriate configuration, the present invention can simultaneously calculate both in-plane and out-of-plane lattice parameters from a single scan.

In the past, reciprocal space mapping of this nature was typically done using a point detector or a line detector, which collected on-axis reflection data. Thus, determination of lattice points outside of the plane of rotation required a physical repositioning of the detector. While more overall information may be collected this way, the repositioning introduces errors in the determination of the relative location of different reflections. It also greatly increases the time necessary to collect a complete data set, which could take many hours or even days. By using a multi-dimensional detector in the present embodiment, this collection time is greatly reduced, and repositioning errors are eliminated. Although the positional relationship between the on-axis and off-axis reflections is non-linear, it is defined by a mathematical relationship (such as is disclosed, for example, in *Two Dimensional X-ray Diffraction*, Bob Baoping He, John Wiley & Sons, Inc., July 2009) and there are no unknown repositioning errors.

The present invention also finds particular application in the analysis of multi-layer crystalline materials. A common example of this is the case of one or more films on an underlying substrate. In such a case, the two different materials will have differences in their crystalline structures that may be represented by overlaid reciprocal lattices. In such a case, the collection of reflection data with a two-dimensional detector integrated over the scan direction, such as in a rocking beam scan as described above, will produce a single image containing data from reflections originating from each of the layers. In such a case, the substrate reflections may be used as a positional reference for the reflections from the film layer.

Figure 3:
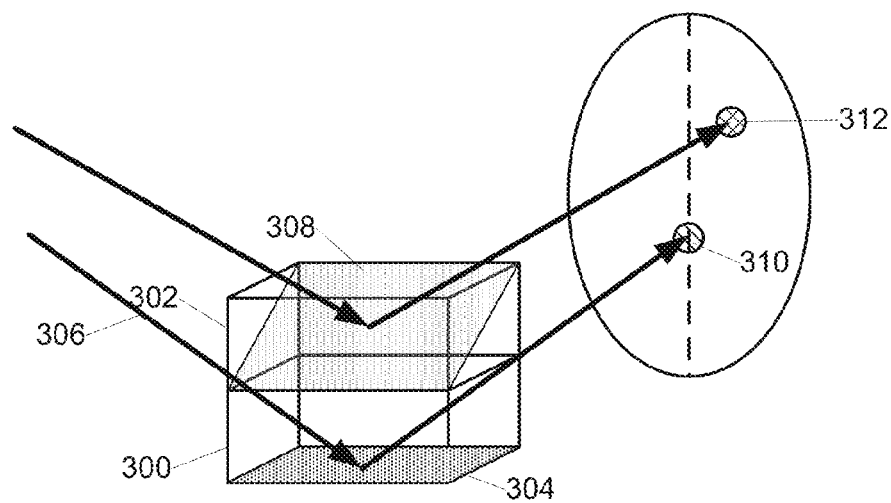
FIG. 3 is a schematic view of the diffraction of an X-ray beam from two different layers of a multiple crystal layer sample material.

FIG. 3 is a schematic depiction of the diffraction of an X-ray beam by a two-layer crystal structure, such as a film on a crystal substrate. A first layer 300, which in this embodiment is a crystal substrate, lies adjacent to a second layer 302, which may be a crystal film on the surface of the substrate 300. While the two layers are shown in the figure as being similar in size, those skilled in the art will understand that this representation is not to scale, and that the film 302 will often be much thinner than the substrate 300. Associated with the substrate layer 300 is a plane 304 of interest within the crystal lattice of the substrate. When this plane passes through the diffracting condition for an incident X-ray beam 306, a reflection 310 is formed that may be measured by an appropriately positioned detector. An atomic plane 308 of the material 302 has gone through a similar diffracting condition during the rocking motion of the incident beam, resulting in reflection 312. By using a two-dimensional detector, a large number of data points for both the substrate layer and the film layer may be collected simultaneously.

In an arrangement like that of FIG. 3, there are reflections generated by each of the two layers. In a conventional detection system the reflection data is collected in separate scans using a point detector or a line detector and, as such, any spatial reference between the reflection data is dependent on the calibration of the diffractometry system and precision of the components involved. In the present invention, however, the collection of on-axis and off-axis reflection data simultaneously with a two-dimensional detector provides a spatial reference between the detected reflections that is not dependent on system calibration. Thus, the reflection data may be processed as if the reciprocal lattices of the two materials were superimposed on each other In one embodiment of the invention, the substrate reflections may be from a known material such as, for example, a silicon (Si) wafer, while the second layer is a film of an unknown material. Using a multi-dimensional detector, a large portion of reciprocal space is then collected simultaneously. By moving the incident angle in a continuous fashion, while maintaining the incident beam to detector angle, a map consisting of the projection of reciprocal space integrated in the incident beam rocking direction can be collected.

Since the reciprocal lattices of the known substrate material and the unknown film material are superimposed, the substrate reflections, in this case the Si wafer reflections, can be used as a standard reference for determination of the precise coordinates, and therefore calculation of the real space lattice constants, of the unknown film material. Because the reflections are being collected in a single frame of reference, the known substrate reflections can be used as a standard even though they do not share the same orientation as that of the unknown film. This is in contrast to conventional methods in which a single vector scan through reciprocal space is used, or a 0D or 1D detector is used to collect a series of points which are post-processed into a planar cross-sectional map through reciprocal space.

As the projections in the foregoing method are a convolution along the incident beam rocking direction, the absolute coordinates in X and Y must be deconvoluted using vector analysis. However, it is often only the magnitude of this vector that is necessary for determining the atomic spacings in the material. Once the raw data has been collected, it can be integrated using known algorithms (such as is disclosed, for example, in *Two Dimensional X-ray*

*Diffraction*, Bob Baoping He, John Wiley & Sons, Inc., July 2009) into a plot of intensity versus 2θ. This plot can then be fit to a model structure using whole pattern fitting techniques as are commonly performed for the analysis of powder materials.

Figure 4:
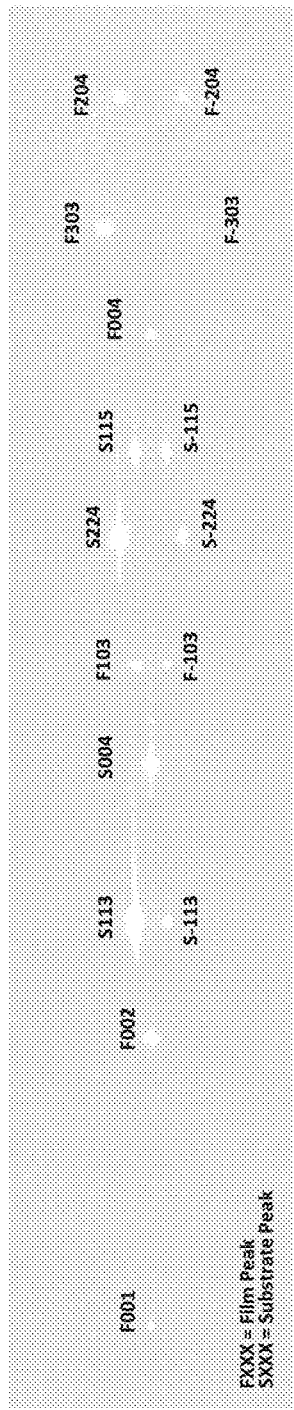
FIG. 4 is a detector image produced diffractometry scan according to the present invention.

FIG. 4 depicts a two-dimensional theta integrated reciprocal space image. Within this image is shown a data series collected from a sample consisting of a known substrate and a functional film layer. The peaks labeled F001, F002, F103/F-103, F004, F303/F-303 and F204/F-204 originate from the film layer, while the peaks labeled S113/S-113, S004, S224/S-224 and S115/S-115 originate from the substrate. The peaks are indexed based on their approximate locations. As known in the art, a family of lattice planes may be identified by three integers (H,K,L) known as the "Miller indices," each index denoting a plane orthogonal to a direction in the basis of the reciprocal lattice vectors. For example, Miller index 100 represents a plane orthogonal to direction "H," index 010 represents a plane orthogonal to direction "K," and index 001 represents a plane orthogonal to direction "L." Thus, the identification of the peaks provides a means to analyze the overall makeup of the substrate and film layers.

In the two-dimensional image of FIG. 4, the peaks along the centerline, having an index of 00L, represent on-axis reflections from the film, and can be used to calculate the out-of-plane lattice parameter. Meanwhile, the off-axis reflections (those having a non-zero value for "H" and/or "K") for both the film and the substrate are also present in the image, and provide useful information regarding the relative crystal orientations and "in-plane" lattice parameters of the substrate and film layers. In conventional diffraction with a 0D or 1D detector, the off-axis reflections would not be in the same frame of reference as the on-axis reflections, and there would therefore be no reference peaks for accurate lattice parameter derivation. However, in the frame collected with the two-dimensional detector of the present invention, the on-axis 00L reflections can be used as a reference for the off-axis reflections. In particular, the presence both above and below the centerline of film peaks for which K=0 (103, 303, 204) and substrate peaks for which H=K (113, 224, 115) indicates that the film has a 45 degree in-plane relationship relative to the substrate.

Figure 5:
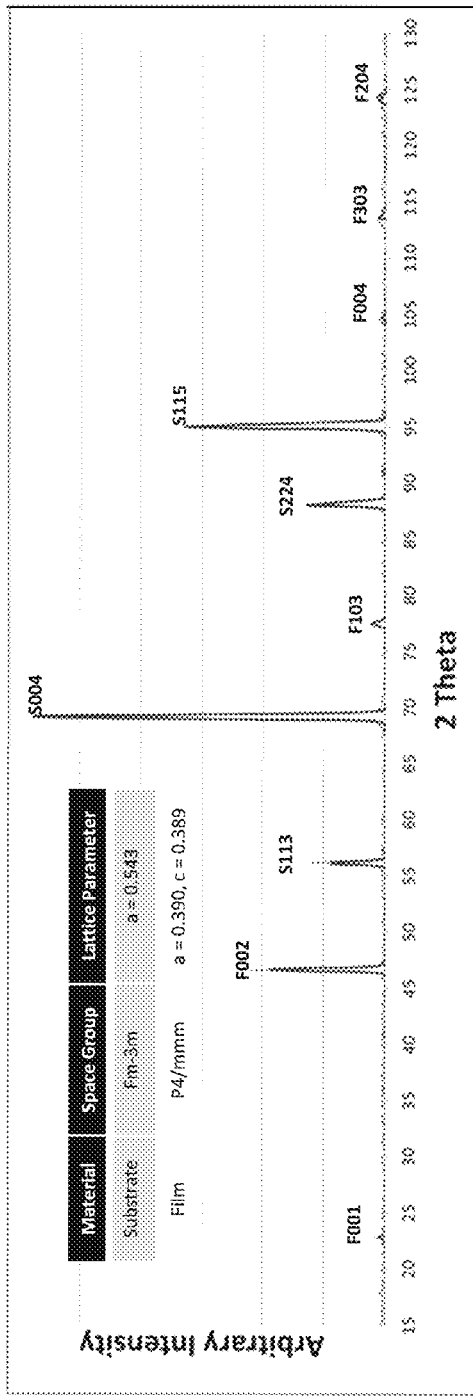
FIG. 5 is a graphical representation of a one-dimensional scan extracted from the data recorded in the image of FIG. 4.

FIG. 5 is a graphical representation of a one-dimensional scan extracted from the data of FIG. 4. The data was integrated into a plot of 2θ versus intensity using known algorithms as described above. In this example, the on-axis and off-axis reflections were then simultaneously fit using the structure analysis software "DIFFRAC.TOPAS" (produced by Bruker AXS, Inc., Madison, Wis.) to determine the in-plane and out-of-plane lattice parameters. A fit for the data was performed assuming a cubic Fm-3m phase for the substrate and a tetragonal p4/mmm phase for the film. Due to the presence of both 00L and HKL reflections in a single frame of reference, both the out-of-plane c-axis lattice parameter and the in-plane a-axis lattice parameter can be refined.

As mentioned above, the lattice parameters of the film and the substrate of foregoing example along with the alignment of the film's K=0 off-axis reflections with substrate's H=K off-axis reflections indicate that there is a 45-degree in-plane relationship between the two layers. These lattice parameters are shown in the table inset of FIG. 5. As indicated, the space group for the substrate is assumed to be a cubic Fm-3m phase, with a lattice parameter a=0.543 nm. The space group for the film is a tetragonal p4/mmm phase, with lattice parameters of a=0.390 and c=0.389. From these parameters, a spatial relationship between the two layers may be predicted. This is demonstrated geometrically in FIG. 5A.

Figure 5A:
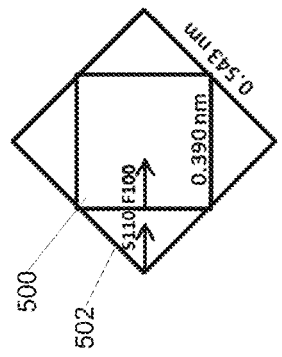
FIG. 5A is a representation of a geometrical relationship between the two crystal layers represented in the image of FIG. 4.

FIG. 5A is a schematic image showing a geometric relationship between the lattice spacings of the substrate and film layers of the foregoing example. The tetragonal class of the film material includes two unit cell parameters that are almost equal, and in the a-b plane the crystal structure is represented by a square shape, as shown by the element 500 shown in the figure, which has a dimension of 0.390 nm along a first side. The cubic form of the substrate (shown as element 502 of FIG. 5A) has sides equal to 0.543 nm, which is geometrically relevant as the diagonal dimension of this form is therefore equal to $\sqrt{2}(0.543)^2$, or 0.768 nm. This value is very close to twice the dimension 0.390 of the film layer and, as shown in FIG. 5A, would approximately fit within the substrate form if rotated at a 45° angle. Due to this geometrical relationship between the lattice parameters of the two layers, it is likely that the film layer will arrange itself at such a 45° orientation relative to the substrate layer, as discussed above.

Those skilled in the art will recognize that, in addition to its applicability to the analysis of a multiple crystal layer sample, the two-dimensional detection method of the present invention may also be used for the determination of the relative crystal orientation of a single crystal material. Thus, for a material such as the substrate represented in the detector image of FIG. 4, the location of the different substrate reflections in the single, two-dimensional image may be used to ascertain the crystal orientation. By comparing the Miller indices of the substrate reflections located along the central axis of the two-dimensional theta integrated reciprocal space image with the Miller indices of the substrate reflections located off the central axis, it is possible to determine certain crystal orientation characteristics. For example, in FIG. 4, the presence of H=K L reflections (i.e., S113, S224 and S115) off the central axis indicates that the H0L or 0KL axis is situated along the scan direction.

While the invention has been shown and described with reference to exemplary embodiments, it will be recognized by those skilled in the art that various changes in form and detail may be made herein without departing from the spirit and scope of the invention as defined by the appended claims.

What is claimed is:

1. A method of performing an X-ray diffraction analysis of a crystal sample, the method comprising:
    illuminating the sample with an X-ray beam from an X-ray source;
    detecting a diffracted X-ray signal emitted from the sample with a multi-dimensional X-ray detector having a fixed position relative to the X-ray source; and
    changing the position of the sample relative to the X-ray source along a scan direction while integrating the diffracted X-ray signal with the detector so as to produce a multi-dimensional image that is compressed in the scan direction, said multi-dimensional image including both on-axis reflections, which lie along a central axis of detection in the multi-dimensional image, and off-axis reflections, which are offset from the central axis.

2. A method according to claim 1 wherein the scan direction is the rocking direction of a goniometer in which the sample is mounted.

3. A method according to claim 1 further comprising identifying Miller indices for the on-axis and off-axis reflections, and determining a relative crystal orientation of the crystal sample by comparing said Miller indices.

4. A method according to claim 1 wherein the sample comprises a plurality of different crystal materials.

5. A method according to claim 4 wherein the different crystal materials include a substrate layer of a first material and a film layer of a second material different than the first material.

6. A method according to claim 4 further comprising integrating data from the multi-dimensional image in a direction perpendicular to the central axis to produce a one-dimensional representation of the on-axis and off-axis reflections from each of the different crystal materials.

7. A method according to claim 6 wherein a first one of the layers is a known reference layer, and wherein said one-dimensional representation is analyzed to determine on-axis and off-axis lattice parameters of a second one of the layers.

8. A method according to claim 1 further comprising constructing a reciprocal space map using the multi-dimensional image.

9. A method of performing an X-ray diffraction analysis of a sample having a plurality of crystal layers each with a different crystalline structure, the method comprising:
  illuminating the sample with an X-ray beam from an X-ray source;
  detecting a diffracted X-ray signal emitted from the sample with a multi-dimensional X-ray detector having a fixed position relative to the X-ray source, such that portions of the diffracted X-ray signal originating from each of the crystal layers are detected at different respective spatial positions on the X-ray detector;
  changing the position of the sample relative to the X-ray source along a scan direction while integrating the detected X-ray reflection signal with the detector so as to produce a multi-dimensional image that is compressed in the scan direction, said multi-dimensional image including both on-axis reflections, which lie along a central axis of detection in the multi-dimensional image, and off-axis reflections, which are offset from the central axis; and
  comparing the reflections within the multi-dimensional image that originate from the different crystal layers to determine a corresponding spatial relationship between the crystalline structures of said layers.

10. A method according to claim 9 wherein the scan direction is the rocking direction of a goniometer in which the sample is mounted.

11. A method according to claim 9 wherein the different crystal materials include a substrate layer of a first material and a film layer of a second material different than the first material.

12. A method according to claim 9 further comprising constructing a reciprocal space map using the multi-dimensional image.

13. An analysis system for performing an X-ray diffraction analysis of a crystal sample, the system comprising:
  an X-ray source that illuminates the sample with an X-ray beam;
  a multi-dimensional detector that detects a diffracted X-ray signal emitted from the sample, the detector having a fixed position relative to the X-ray source; and
  a scan mechanism that changes the position of the sample relative to the X-ray source along a scan direction while the diffracted X-ray signal is integrated by the detector so as to produce a multi-dimensional image that is compressed in the scan direction, said multi-dimensional image including both on-axis reflections, which lie along a central axis of detection in the multi-dimensional image, and off-axis reflections, which are offset from the central axis.

14. An analysis system according to claim 13 wherein the sample is mounted in a goniometer and the scan direction is the rocking direction of the goniometer.

15. An analysis system according to claim 13 wherein the sample comprises a plurality of different crystal materials.

16. An analysis system according to claim 15 wherein the different crystal materials include a substrate layer of a first material and a film layer of a second material different than the first material.

* * * * *